US006383502B1

(12) United States Patent
Dunshee et al.

(10) Patent No.: US 6,383,502 B1
(45) Date of Patent: *May 7, 2002

(54) NON-STINGING COATING COMPOSITION

(75) Inventors: Wayne K. Dunshee, Maplewood; Gilbert L. Eian, Mahtomedi, both of MN (US)

(73) Assignee: 3M Innovative Properties Company, St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/533,136

(22) Filed: Mar. 23, 2000

Related U.S. Application Data

(60) Provisional application No. 60/126,154, filed on Mar. 25, 1999.

(51) Int. Cl.[7] .............................. A61K 6/00; A61K 7/00
(52) U.S. Cl. ...................... 424/401; 424/59; 424/63; 424/78.02; 424/78.03
(58) Field of Search ............................ 424/401, 59, 63, 424/76.3, 78.02, 78.03

(56) References Cited

U.S. PATENT DOCUMENTS

| | | | |
|---|---|---|---|
| 4,987,893 A | 1/1991 | Salamone et al. | 128/156 |
| 5,103,812 A | 4/1992 | Salamone et al. | 602/52 |
| 5,376,294 A | 12/1994 | Izuho et al. | |
| 5,376,378 A | 12/1994 | Li et al. | 424/448 |
| 5,468,477 A * | 11/1995 | Kumar et al. | 424/78.17 |
| 5,616,598 A * | 4/1997 | Lion et al. | 514/374 |
| 5,804,173 A * | 9/1998 | Hutchins et al. | 424/70.16 |
| 5,916,547 A * | 6/1999 | Torgerson et al. | 424/70.12 |

FOREIGN PATENT DOCUMENTS

| | | | |
|---|---|---|---|
| EP | 0 409 550 | 1/1991 | A61L/25/00 |
| EP | 0 572 416 B1 | 12/1993 | A61F/13/02 |
| EP | 0 918 069 | 5/1999 | C08L/43/04 |
| JP | 11181003 A2 * | 12/1997 | |
| WO | WO 88/05060 | 7/1988 | C08F/30/08 |
| WO | WO92/14428 | 9/1992 | A61F/13/00 |
| WO | WO 98/58624 | 12/1998 | A61K/7/32 |

OTHER PUBLICATIONS

"Standard Practice for Dilute Solution Viscosity of Polymers", *American Society for Testing Materials* D–2857–95 (1995) pp. 149–153.

Billmeyer, "Solution Viscosity and Molecular Size", *Textbook of Polymer Science*, New York, Wiley (1971) pp. 84–85.

Collins et al., "Polymer Characterization Techniques", *Experiments in Polymer Science*, (1964) pp. 146–153.

No–Sting Skin–Prep™, Smith & Nephew, Inc., Florida (1997).

International Cosmetic Ingredient Dictionary Handbook, vol. 1, 7th ed., pp. 605, 675 and 676, 1997.

International Preliminary Examination Report, PCT/US00/07752, dated Apr. 19, 2001.

* cited by examiner

*Primary Examiner*—Thurman K. Page
*Assistant Examiner*—Liliana Di Nola-Baron
(74) *Attorney, Agent, or Firm*—Doreen S. L. Gwin

(57) ABSTRACT

Compositions comprising 1–40% siloxane containing polymer; 60–99% of an Alkane-Based Siloxy Polymer Reaction Solvent, and 0–15% of adjuvants are useful for application to the skin or as components in cosmetic or topical medicament compositions.

12 Claims, No Drawings

US 6,383,502 B1

NON-STINGING COATING COMPOSITION

This application claims priority to U.S. Provisional Patent Application No. 60/126,154, filed Mar. 25, 1999.

FIELD OF THE INVENTION

This invention relates to coating compositions and compositions to be used as additives. More specifically, this invention relates to siloxy-polymer containing compositions in a solvent, wherein the composition does not sting on application to the skin of a user.

BACKGROUND

Coating compositions are desired in the art, both as skin protecting compositions and medicament containing compositions.

U.S. Pat. Nos. 5,103,812 and 4,987,893 relate to a conformable bandage and coating materials. These materials are combinations of alkylsiloxy silicone containing polymers admixed with liquid polydimethylsiloxanes. Polymers of these compositions are incorporated into a solvent system that is preferably polydimethylsiloxane having the solubility parameter of 6.8–7.2 $[cal/cm^3]^{1/2}$. See column 5, lines 50–55. These polymer films are also said to be able to be cast from liquids containing good solvents with solubility parameters of between about 9 to 10 $[cal/cm^3]^{1/2}$. Specific examples of such solvents are tetrahydrofuran and ethylacetate. See column 6, lines 50–54.

SUMMARY OF THE INVENTION

A composition for application to the skin, comprising: 1–40% siloxane containing polymer; 60–99% of an Alkane-Based Siloxy Polymer Reaction Solvent, and 0–15% of adjuvants is provided.

A method of making a siloxane-containing polymer is also provided comprising vinyl containing alkylsiloxysilanes alone or as co-, ter- or multi component polymers including other polymerizable monomers, which method comprises undertaking the polymerization in an alkane solvent selected from the group consisting of $C_5$—O—$_5$—$C_9$ straight, branched or cyclic alkanes so that the reaction provides a composition having a polymer content greater than 15% by weight.

Aqueous gel compositions are also provided.

DETAILED DESCRIPTION OF THE INVENTION

No-sting skin protectants are described in U.S. Pat. Nos. 5,103,812 and 4,987,893, but these materials cannot be provided at higher solids than 15% without becoming very stringy and pituitous. At higher solids content, the polymer will not spread when painted onto the skin from the described formulation. Furthermore, the method for applying thick coatings to the skin as described in the prior art is through multiple applications of thin coatings. In the prior art method, towelette wipes having solutions comprising 10% polymer content are applied over areas to be treated and dried. By the time the coating is dry on the skin, the applicator wipe may be also dry and a new wipe must be used.

Surprisingly, it has been found that non-stinging coating compositions may be provided utilizing a siloxy polymer, but which is cast from a solvent not previously thought to be appropriate for such use. Optionally, the polymer content of the inventive compositions may be significantly higher than the polymer content possible in prior art compositions, while maintaining good handleability properties.

More specifically, the solvent system for the compositions of the present invention is selected such that it is an Alkane-Based Siloxy Polymer Reaction Solvent. An Alkane-Based Siloxy Polymer Reaction Solvent is a solvent system that primarily contains straight, branched or cyclic alkanes, and is capable of acting as the reaction solvent (i.e. the non-reactive fluid portion of a reaction composition) for the polymerization reaction of the specific monomer composition of TRIS/Methyl Methacrylate/2-Ethylhexyl acrylate in a 53/39/8 weight ratio. The solvent system is readily identified in a routine evaluation by undertaking a polymerization reaction using the specific monomer composition described above under a Standard Polymerization Reaction as defined below.

A Standard Polymerization Reaction comprises reacting 20% total monomer concentration by weight based on monomer plus solvent with VAZO 67 free radical initiator used at 0.3% by weight based on total monomer at a reaction temperature of 70° C. under nitrogen for 36 hours (or less time if greater than 90% monomer conversion has occurred). A solvent system is deemed to be an Alkane-Based Siloxy Polymer Reaction Solvent if, after cooling to room temperature, the reacted composition yields a clear, pourable solution of polymer, and the inherent viscosity ("IV" as tested by ASTM D2857-95 at 25° C. and according to principles discussed in Experiments in Polymer Science, by Edward A. Collins, Jan Bares and Fred W. Billmeyer, New York, Wiley (1973) pp 146–153.) of the polymer product is measured in ethyl acetate solvent at a nominal solids concentration of 0.5% (w/v)is less than 0.5 dl/g. Solvents which yield polymer with inherent viscosity greater than 0.5 dl/g are unsuitable.

A specific procedure for the test is detailed below.

A mixture of 4.24 g TRIS, 3.12g methyl methacrylate and 0.64g 2-ethyl hexyl acrylate is dissolved in 32 g of solvent in a 4 oz narrow mouth flint glass bottle and 0.024 g of VAZO 67 is added. The solution is purged with nitrogen at a flow rate of 1 liter/ minute for two minutes to remove dissolved oxygen. The bottle is closed tightly with a teflon lined metal cap and placed in a launder-o-meter preset at 70° C. for at least 24 hours. Conversion is determined from measurement of percent non volatile solids by loss on drying at 105° C. for 60 minutes.

Preferred solvents of the present invention are selected from one or more $C_5$–$C_{12}$ straight, branched, or cyclic alkanes. Particularly preferred solvents are methylcyclopentane; n-heptane; n-octane; n-nonane; 2,2,4-trimethyl pentane; 3,4-dimethyl hexane. The solvent system may also comprise a blend of solvents that are a mixture of straight, branched or cyclic C10–C12 alkanes with one or more $C_5$–$C_9$ straight, branched or cyclic alkanes.

For example, preferred solvent blends include mixtures of one or more of n-decane, n-undecane or n-dodecane with one or more of methylcyclopentane; n-heptane; n-octane; n-nonane; 2,2,4-trimethyl pentane; 3,4-dimethyl hexane.

The present inventive compositions are preferably provided as a skin protecting conformable bandage that is painted on. Alternatively, the compositions of the present invention may be provided as a component in a cosmetic or medicament containing composition.

The liquid polymer-containing coating materials of this invention comprise a siloxane containing polymer and a solvent system which is non-stinging to a user. Preferably the polymer is present from 1 to 40% by weight and the solvent is present in amounts of 60 to 99%. The material forms a coating or bandage in the form of a dried film when applied to a surface or the skin of a user.

Advantageously, the present invention provides the ability to manufacture the polymer in the same solvent as used in the final formulation. It has been found that it is exceedingly difficult to manufacture this polymer in the prior art solvent system hexamethyl disiloxane ("HMDS"). The ability to manufacture in the same solvent as the ultimate product is a significant advantage in cost savings, and additionally provides a more complete distribution of reaction products that may aid in film formation.

Use of the solvent system of the present invention allows for incorporation of higher solids content of the polymer, and also allows for selection of the polymer formulation to provide suitable materials for the desired use at lower siloxy silane component content.

It has surprisingly been found that the alkane solvents as described herein may be highly effective cosolvents with volatile siloxane (such as HMDS), which can substantially increase the amount of solids content that may be obtained without becoming pituitous. Additionally, it has been found that the addition of about 5%–10% of Tea Tree Oil (oil of Melaleuca alternifolia) and the like similarly increases the amount of solids content that may be obtained without becoming pituitous.

Preferably, the siloxane containing polymer comprises at least one vinyl containing alkylsiloxysilane and an addition polymerizable comonomer.

It is a feature of the invention that the liquid materials can act at room temperature (20° C.) when applied to skin, nails, or mucous membranes of a user to form films in minutes or less, which films are excellent bandages. The films are conformable, comfortable and can be elastic and flexible. The films do not irritate the skin and mucous membrane when sprayed or deposited in any way during application and in use after drying. The bandages are substantially painless and can be easily removed substantially without pain. The dried bandages formed are substantially non-water sensitive, and waterproof and have high water vapor and oxygen gas transmission therethrough. The bandages form when applied over surfaces wet with water, blood or body fluids, in short times at standard room temperature and reasonable variants thereof. The liquid composition and/or dried polymer film can have various medicaments or other agents incorporated therein for maintaining sterility and/or for release to the underlying area of the body of a user. For example, perfumes, antimicrobial, botanicals, medicants, or similar materials can be released from the coatings.

The siloxane containing polymers of this invention can comprise vinyl containing alkylsiloxysilanes alone or as co-, ter- or multi-component polymers which can include other polymerizable monomers that do not make the polymers hydrophilic.

Typical vinylaklylsiloxysilanes that may be utilized are:
3-methacryloyloxypropyltris(trimethylsiloxy)silane (TRIS);
3-methacryloyloxypropylpentamethyldisiloxane;
3-methacryloyloxypropylbis(trimethylsiloxy)methylsilane;
3-acryloyloxypropylmethylbis(trimethylsiloxy)silane;
3-acryloyloxypropyltris(trimethylsiloxy)silane; and others.

Typical addition polymerizable monomers which may be reacted with the vinylalkylsiloxysilanes to form multi component polymers are: methyl methacrylate methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, isodecyl acrylate, isodecyl methacrylate, isooctyl acrylate, isooctyl methacrylate, isobornyl acrylate, isobornyl methacrylate, benzyl methacrylate, 2-butoxyethyl acrylate, n-butyl acrylate, n-butyl methacrylate, ethyl acrylate, ethyl methacrylate, dimethyl itaconate, di-n butyl itaconate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, methyl acrylate, alpha methyl styrene, styrene, p-t-butyl styrene, 4-methoxystyrene, n-octadecyl acrylate, n-otadecyl methacrylate, 2-phenylethyl methacrylate, n-tridecyl methacrylate, vinyl benzoate, vinyl naphthalene. In addition, fluorinated siloxanes, fluorinated itaconates, fluorinated methacrylates or acrylates, such as hexafluoroisopropyl methacrylate, can be used.

Any hydrophobic polymerizable monomer can be used as long as the resulting copolymer has desired $O_2$ and $H_2O$ vapor permeability. These additional polymerizable comonomers can be present in amounts up to 0.85 mole fraction.

The polymers of the invention are preferably in proportions between about 15–100 mole % vinylalkylsiloxysilane which component maintains the desired compatibility of the polymer in the volatile liquid polydimethylsiloxanes with polar adjuvants, provides high moisture and oxygen permeability, and provides biocompatibility. A range of 20 to 40 mole % of the vinylalkylsiloxysilane in the polymer is preferred in the polymer of this invention. Other addition polymerizable monomers may be copolymerized with the vinylalkylsiloxysilanes between about 0–85% mole of the polymer composition to adjust permeability, adhesion, toughness, elasticity, temperature stability, and impact resistance, among other film qualities.

The polymers may be linear, branched, or slightly cross-linked and can be homo, co-, ter- or multi polymers. They may be random copolymers or segmental in nature.

Typical vinylalkylsiloxysilane monomers can have the following formulas:
$CH_2\!=\!C(R^1)COOR^2SiR^3R^4R^5$ Where
$R^1\!=\!H$,
$CH_3$, or
$CH_2COOR'$,
Where $R^2\!=\!$alkyl ($C_1$–$C_4$) or 
Where $R^3$, $R^4$, $R^5\!=\!OSi(Y)_3$, or alkyl ($C_1$–$C_6$),
Wherein, at least one of $R^3$, $R^4$, $R^5\!=\!OSi(Y)_3$
Where
Y=alkyl ($C_1$–$C_6$), $OSi(Z)_3$ or
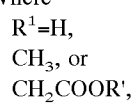
Where Z=alkyl ($C_1$–$C_6$), aryl, and
Where $R'\!=\!R^2SiR^3R^4R^5$ The polymers may have molecular weights from 50,000 to several million. The preferred molecular weight range is 50,000 to 500,000 weight average molecular weight. Lower molecular weight polymers have notably higher solubility in the solvents and solvent systems of this invention and hence, while they can be film formers, they generally are slow to dry and remain tacky. The molecular weight of the polymers may be controlled by varying initiator, initiator concentration, reaction temperature, reaction solvent, and/or reaction method.

Most preferably, the polymers of the invention are acrylate or methacrylate terpolymers having an A monomer component that is a silane derivative, a B monomer component that when provided as a homopolymer would prepare a "hard" polymer, and a C monomer component that, when provided as a homopolymer would prepare a "soft" polymer.

For the A monomer, examples of the silane derivatives are as described above. B monomers are "hard" where the corresponding homopolymer typically has a glass transition temperature ($T_g$) of more than about −5° C. Examples of such monomers are acrylate or methacrylate monomers, preferably $C_1$–$C_4$ alkyl methacrylates. Most preferably, the hard monomer is methyl methacrylate.

Other examples of monomers that can be used for the hard monomer component are monomers having the requisite $T_g$ values including methacrylates having a structure other than delineated above, such as benzyl methacrylate and isobornyl methacrylate methcrylamide such as N t butylmethacrylamide; acrylates such as isobornyl acrylate; acrylamides such as N butylacrylamide and N-t butylacrylamide; diesters of unsaturated dicarboxylic acids such as diethyl itaconate and diethyl fumarate; vinyl nitriles such acrylonitrile and methacrylonitrile; vinyl esters such as vinyl acetate and vinyl propionate; and monomers containing an aromatic ring such as styrene; α-methyl styrene and vinyl toluene. 'C' monomers may be selected from monomers that form soft homopolymers. "Soft" monomers are monomers where the corresponding homopolymer typically has a $T_g$ of less than about 10° C., provided that the hard monomer has a higher $T_g$ than the soft monomer in each polymer. Such monomers are $C_4$–$C_{12}$ alkyl acrylates and $C_6$–$C_{12}$ alkyl methacrylates, wherein the alkyl groups are straight, branched, or cyclic. Most preferably, the soft monomer is selected from $C_7$–$C_{10}$ straight chain alkyl acrylates.

Other examples of monomers that can be used for the soft monomer component are monomers having the requisite $T_g$ values including dienes, such as butadiene and isoprene; acrylamides, such as N-octylacrylamide; vinyl ethers such as butoxyethylene, propyloxyethylene and octyl oxyethylene; vinyl halides, such as 1,1-dichloroethylene; and vinyl esters such as vinyl caprate and vinyl laurate.

It has been found that this mix of monomers provide particularly advantageous abilities to adjust mole fraction ratios to optimize oxygen permeability, ductility, moisture vapor transmissibility of the film and cost of materials. Highly durable coatings are particularly desired to enable the coating to remain on the skin for an extended time and to provide superior protection.

Most preferably, the siloxane-containing polymer comprises about 50 to 60 weight percent A monomer, 25–45 weight percent B monomer, and about 3 to 20 weight percent of C monomer. A specifically preferred embodiment is where the siloxane-containing polymer comprises about 50 to 60 weight percent of 3-methacryloxypropyl tris (trimethylsiloxy)silane, about 25 to 45 weight percent methyl methacrylate, and about 3 to 20 weight percent of a monomer selected from $C_7$–$C_{10}$ straight chain or branched alkyl acylates.

Particularly preferred siloxane-containing polymers have an overall effective Tg of 20–80%, more preferably 40–70%, and most preferably 50–60° C.

One variation in selection of monomers to be used in siloxane containing polymer is using more than one monomer within each category A, B, or C. For example, the polymer could comprise 57% 3-methacryloyloxypropyl tris (trimethylsiloxy)silane, 39% methyl methacrylate, 2% isooctyl acrylate and 2% decyl acrylate. The last two monomers each satisfy the definition of the C monomer, and together provide the desired quantity of this component.

Any free radical initiator can be used in forming the polymers including azobisisobutyronitrile; 2,2'-azobis(2,4 dimethylpentane nitrile); 2,2'-azobis-(2-methylbutane nitrile); potassium persulfate; ammonium persulfate; benzoyl peroxide; 2,5-dimethyl 2,5-bis(2-ethylhexanoylperoxy) hexane; and the like. The polymerization can be carried out by solution, emulsion, or suspension techniques.

Preferably, a polymer comprised of methyl methacrylate, isooctyl acrylate, and ("3-methacryloxypropyl tris (trimethylsiloxy)silane) ("TRIS") is polymerized directly in a composition of 90% 2,2,4-trimethylpentane with 10% 3,4-dimethylhexane (Permethyl® 97A from Permethyl Specialties, LLC, Milmay, N.J.) or n-heptane at 25% nonvolatile finished polymer.

Adjuvants of the present compositions may comprise cosolvents, suspending aids, preservatives, antioxidants, active ingredients such as medicaments, humectants, emollients, slipagents, waxes, colorants (including dyes, pigments, colored particles, glitter and the like), flavorants, fragrances and the like. Adjuvants may also include solid materials, such as titanium dioxide and silica. Such materials may reduce tackiness of the overall composition, and additionally may perform a function such as acting as a sunscreen, handling modifier or to modify composition drying rates.

Preferred cosolvents that may be used as adjuvants of the present compositions include alcohols, ketones, oils and the like. Preferably, these cosolvents are present in an amount such that they do not render the overall composition to have a stinging effect upon application to the skin.

The high solids polymer is useful as a skin protectant paint and is compatible with a variety of useful adjuvants such as aloe vera in mineral oil, vitamin E, vitamin A, palmitate, triclosan, methyl salicylate, menthol, capsicum oleoresin, tea tree oil, squalane, peppermint, citronella, spearmint, jojoba oil, sweet almond oil, other oil and oil soluble materials. Using oils with higher carbon chains will vary the evaporation rates and/or skin absorption rates and provide short term plasticizing of the polymer, which in turn gives the polymer coating a glossy visible appearance until the solvent evaporates and/or absorbs.

The compositions of this invention may be applied to the skin, mucous membranes, etc. in liquid form by utilization of an applicator, such as a brush, rod, finger, sponge, cloth, dropper, etc; in spray or mist form; or any other usable technique for applying a liquid to a surface.

Surprisingly, compositions of the present invention may be formulated to provide excellent sprayable siloxane-polymer containing compositions. A sprayable composition may surprisingly be provided having a polymer content of as high as 6–10% by weight.

Medicants may be incorporated into the liquid or solid, dried film bandages for ready or continual release as the invention provides for an inert, longlasting, highly permeable film which can contain medicant or other active agents to be applied to the skin, mucous membranes and other body areas on which it is desired to release the active agent over an extended period of time. Examples of useful medicants are fungicides, pesticides, antimicrobial agents, antiviral agents, antitumor agents, blood pressure and heart regulators, and many more. Other types of active agents which may be desirable to incorporate include perfumes, plant growth regulators, DEET, plant insecticides, UV and IR absorbers, etc.

Compositions of the present invention provide a treatment benefit to the cells of the skin. Particularly, compositions to the present invention can have a beneficial affect for the treatment of dry or irritated skin. Compositions of the present invention that have high solid content are particularly advantageous because they can be more easily observed after placement on the skin. These compositions tend to be easier to coat in thicker layers, which are more visible. Films formed by the compositions of the present invention are highly substantive, flexible and non-tacky. They tend to provide enhanced benefit to dry skin because they decrease the water loss from the skin. Additionally, the films tend to fill in cracks, fissures, and other damaged surfaces of the skin.

Compositions of the present invention may optionally incorporate pigments, glitters, opalescent materials and or surface optical brighteners, which may be added to the composition or suspended in the polymer solvent mix. The material may be redispersed with the help of hand agitation or using a mixing ball in the dispensing container, as is common in fingernail polishes and make-up containers. The compositions of this invention could be used for applications other than medical body care. For instance, the coating could be used as a water repellent, yet $H_2O$ vapor permeable, film applied to sanitary napkins, diapers, or panties. With the incorporation of mildewcides, the coating could be used to cover grout in tiled surfaces. The present compositions are further useful as a sunscreen with the incorporation of UV absorbers. Still other uses include forming films for use in eliminating chapped lips, treating skin and internal body surfaces, and providing protection to skin and other surfaces which may be medicated prior to application.

The present invention also provides unique compositions to be used as a minor component of a larger cosmetic composition. More specifically, a method of formulating cosmetics is provided, comprising utilizing a composition of the formula:

a) 1–40% of siloxane-containing polymer;
b) 60–99% of an Alkane-Based Siloxy Polymer Reaction Solvent; and
c) 0–10% of adjuvants;

As an ingredient in a cosmetic formulation. This method provides a stable and cost-effective system for introducing siloxane-containing polymers in beneficial amounts into cosmetic formulations, wherein the polymer need be present as only a small fraction of the overall cosmetic formulation. Such formulations include cosmetics such as facial and body powders, hair spray, shampoo and conditioner products, lotions, creams, mascaras, eye liners, nail polish, body paints, and the like. Cosmetic compositions of the present invention may include nail polishes, scar hiding compositions, waterproof eyeliners, skin covering make-up base, and skin crack fillers and sealers. Cosmetic compositions may be provided in the form of compacted powders, lotions, creams, gels, sticks, and the like. Additional cosmetic compositions include treatment for the hair, including styling aids, creams, gels, lotions, sprays, and the like. Compositions of the present invention may additionally find advantageous use as lipsticks.

In another embodiment of the present invention, a stable water based non-flammable emulsion is provided of the skin protectant polymer. Surprisingly, this formulation yields equivalent skin protection to the solvent-based polymer composition, and additionally dries in a suitable time frame that is similar to the more volatile solvent based system. Advantageously, the gel may be massaged into the skin until nearly dry for additional therapeutic benefits. Additionally, such compositions may be easier to use with protective gloves that are adversely affected by solvent-based compositions.

Preferred gel compositions comprise (a) 1–15% siloxane-containing polymer, (b)10–25% Alkane-Based Siloxy Polymer Reaction Solvent, (c) 0–10% adjuvants, (d) 38–88.5% water, and (e) 0.5–2 emulsifier.

The emulsion gel may optionally contain therapeutic ingredients in both the solvent oil and water phases. Examples of such ingredients are as follows:

| Oil/Solvent Phase Therapeutic Ingredients: | | |
|---|---|---|
| Methyl Salicylate | Spearmint | Aloe Vera Oil Extract |
| Menthol | Sweet Almond Oil | Vitamin E |
| Capsicum | Jojoba Oil | Vitamin A |
| Tea Tree Oil | Citronella | Vitamin A Palmitate |
| Peppermint | Squalane | Triclosan |
| Vitamin C ester | | |

| Water Phase Therapeutic Ingredients: | |
|---|---|
| Vitamin C | Quaternium 15 |
| Aloe Vera | Germaben II |
| Witch Hazel | |

The following examples are provided for purposes of illustrating the present invention, and are not intended to be limiting of the broadest concepts of the present invention. Unless otherwise indicated, all parts and percentages are by weight and all molecular weights are weight average molecular weight.

EXAMPLES

Preparative Example 1

Polymer Preparation

A mixture of monomers, 3-methacryloxypropyltris (trimethyl siloxy)silane known as TRIS, methyl methacrylate (MMA) and isooctyl acrylate (IOA) in a 53/39/8 weight ratio were dissolved in isooctane(2,2,4-trimethyl pentane, purchased as Permethyl® 97A and commercially available from Permethyl Specialties, LLC, Milmay, N.J.) at 25% total monomer by weight. Initiator (Vazo 67, DuPont) was added at 0.3 weight percent based on total monomer. The solution was purged with nitrogen to remove oxygen and heated to 70° C. for 72 hours. Monomer conversion determined by loss on drying was >97%.

Preparative Example 2

22% Solids Polymer Composition

A polymer was prepared as described in Example 45 of U.S. Pat. No. 5,103,812, the disclosure of which is hereby incorporated by reference. This dry polymer was dissolved in a solution of 10% solids in HMDS, and this solution was further diluted with 2% of polymethylphenyl siloxane and solvent was removed by evaporation to a final solids content of 22%.

Preparative Example 3

24% Solids Polymer Composition

A polymer was prepared as described in Example 45 of U.S. Pat. No. 5,103,812, the disclosure of which is hereby incorporated by reference. This dry polymer was dissolved in a solution of 10% solids in HMDS, and this solution was further diluted with 2% of polymethylphenyl siloxane and solvent was removed by evaporation to a final solids content of 24%.

Preparative Example 4

25% Solids Polymer Composition

A polymer was prepared as described in Example 45 of U.S. Pat. No. 5,103,812, the disclosure of which is hereby incorporated by reference. This dry polymer was dissolved in a solution of 10% solids in HMDS, and this solution was further diluted with 2% of polymethylphenyl siloxane and solvent was removed by evaporation to a final solids content of 25%.

Preparative Example 5

100% Solids Polymer Composition

A polymer was prepared as described in Example 45 of U.S. Pat. No. 5,103,812, the disclosure of which is hereby incorporated by reference. This dry polymer was dissolved in a solution of 10% solids in HMDS, and this solution was further diluted with 2% of polymethylphenyl siloxane and solvent was removed by evaporation to a final solids content of 100%.

Example 1

4.35 g of the composition of Preparative Example 2
0.50 g Tea Tree Oil
0.10 g Peppermint Oil

Example 2

4.75 g of the composition of Preparative Example 2
0.25 g Spearmint

Example 3

4.75 g of the composition of Preparative Example 2
0.25 g Citronella Oil

Example 4

4.45 g of the composition of Preparative Example 3
0.5 g Tea Tree Oil
0.5 g Vitamin E

Example 5

4.5 g of the composition of Preparative Example 2
0.5 g Exxsolv D40 solvent

Example 6

4.5 g of the composition of Preparative Example 2
0.35 g Exxsolv D40
0. 10 g Vitamin E mixed Tocopheral
0.05 g Methyl Salicylate

Example 7

8.9 g of the composition of Preparative Example 4
0.9 g Exxolv D40
0.21 g Squalane
0.25 g Vitamin E

Example 8

8.8 g of the composition of Preparative Example 4
0.9 g Exxsolv D40
0.1 g Tea Tree Oil
0.10 g Vitamin E
0.1 g Squalane

Example 9

1.0 g of the composition of Preparative Example 5
3.0 g Permethyl 97A
easily dissolved into non-stringy fluid.

Example 10

39.67 g of the composition of Preparative Example 1
9.08 g Permethyl 97A
0.50 g polymethylphenyl siloxane
0.25 g Actiphyte Aloe Lipo
0.25 g Vitamin E 4-80
0.25 g Trislosan

Example 11

45.75 g of the composition of Preparative Example 1
2.5 g Tea Tree Oil
1.0 g polymethylphenyl siloxane
0.25g Aloe Lipo
0.25 g Vitamin E 4-80
0.25 g Triclosan Application of high solids polymer in the above formulations allowed for a highly substantive coating for protection of skin cracks and skin lesions.

Gels according to the present invention may be made as follows:

Preparative Example 6

Emulsion Premix
0.3% BF Goodrich Pemulin TR2
0.3% Carbopol 980
0.25% Germaben II
99.15% Water With high shear mixing, Pemulin TR2 and Carbopol 980 are added to water, and mixing is continued until polyacrylic acids are well dispersed and no lumps are visible. Germaben II preservative is slowly added.

Example 12

10.0 g of the composition of Preparative Example 6
2.5 g of the polymer prepared as described in Example 45 of U.S. Pat. No. 5,103,812
0.12 g 50% Triethanolamine in water
10 grams of the composition of Preparative Example 6 as stirred with a high shear impeller, and 2.5 grams of the polymer was slowly added and mixed for
1.0 min. The gel was neutralized with addition of 0.12 grams of 50% TEA while stirring. The gel thickened and stirring was discontinued.

Preparative Example 7

Polymer Solution Composition

A polymer was prepared as described in Example 45 of U.S. Pat. No. 5,103,812, the disclosure of which is hereby incorporated by reference. This dry polymer was dissolved in a solution of 10% solids in HMDS, and this solution was further diluted with 2% of polymethylphenyl siloxane.

Example 13

10 g of the composition of Preparative Example 6
2.5 g of the composition of Preparative Example 7
0.12 g 50% TEA
10 grams of the composition of Preparative Example 6 was stirred with a high shear impeller, and 5 g of the composition of Preparative Example 7 was slowly added and mixed for 1.0 min. The composition was neutralized by addition of 0.12 grams of 50% TEA while stirring. A thickened gel formed, and stirring was discontinued.

Preparative Example 8

20% Solids Polymer Composition

A polymer was prepared as described in Example 45 of U.S. Pat. No. 5,103,812, the disclosure of which is hereby incorporated by reference. This dry polymer was dissolved in a solution of 10% solids in HMDS, and this solution was further diluted with 2% of polymethylphenyl siloxane and solvent was removed by evaporation to a final solids content of 20%.

Example 14

10 g of the composition of Preparative Example 6
5 g of the composition of Preparative Example 8
0.12 g50% TEA

Example 15

10 g of the composition of Preparative Example 6 added after combined:
   3.8 g of the composition of Preparative Example 7
   0.2 g Tea Tree Oil
   Neutralize with 0.12 grams 50% triethanolamine make as in Example 12.

Example 16

Water Phase:
10 g of the composition of Preparative Example 6
   0.1 g Witch Hazel Extract
Oil Phase:
   4.23 g of the composition of Preparative Example 7
   0.225 g Tea Tree Oil
   0.045 g Vitamin E
   Combine oil phase to water phase with high shear agitation. Neutralize with 0.12 g 50% triethanolamine solution.

Example 17

10 g of the composition of Preparative Example 6
5 g 89% of the composition of Preparative Example 3
   10% Tea Tree Oil
   1% Vitamin E
0.12 g 50% TEA solution

Example 18

20 g of the composition of Preparative Example 6
4 g 89% of the composition of Preparative Example 3
   10% Tea Tree Oil
   1% Vitamin E
0.24 g 50% TEA solution

Example 19

30 g of the composition of Preparative Example 6
12 g of a composition as follows:
   19.3% of the composition of Preparative Example 1
   2% Tea Tree Oil
   0.5% Aloe Oil
   0.5% Vitamin E
   0.5% Triclosan
   77.2% Permethyl 97A
0.36 g 50% TEA solution

Example 20

30 g of the composition of Preparative Example 6
12 g of a composition as follows:
   23% of the composition of Preparative Example 1
   5% Tea Tree Oil
   2% polymethylphenyl siloxane
   0.5% Aloe Lipo
   0.5% Vitamin E 4-80
   0.5% Triclosan
   68.5% Permethyl 97A
0.36 g 50% Triethanolamine solution

Example 21

4 g Preparative Example 1
0.7 g Permethyl 97A
0.3 g Chromalite Red (pigment from Mallinckrodt, Inc., St. Louis, Mo.)
Provided a substantive cosmetic skin paint.

Example 22

30 g of the composition of Preparative Example 6
12 g of a composition as follows:
   19.3% of the composition of Preparative Example 1
   2% Tea Tree Oil
   0.01% esterified Vitamin C
   0.5% Vitamin E
   0.5% Triclosan
   77.69% Permethyl 97A
0.36 g 50% TEA solution
To 6 parts of Chromalite Brown pigment was added 94 parts of the above emulsion, which provided a stable gel body paint.

Preparative Example 9

Polymer Preparation

A mixture of monomers, 3-methacryloxypropyltris(trimethyl siloxy)silane known as TRIS, methyl methacrylate (MMA) and isooctyl acrylate (IOA) in a 53/39/8 weight ratio were dissolved in n-heptane at 25% total monomer by weight. Initiator (Vazo 67, DuPont) was added at 0.3 weight percent based on total monomer. The solution was purged with nitrogen to remove oxygen and heated to 70° C. for about 60 hours. Monomer conversion determined by loss on drying was >97%.

Example 23

40.00 g of the composition of Preparative Example 1
1.00 g of Tea Tree Oil
0.25 g Vitamin E 4-80 (Eastman Chemical, Kingsport, Tenn.)
0.25 g Triclosan
0.025 g Oil soluble Vitamin C ester
8.475 g Permethyl 97A

Example 24

10 g of Preparative Example 6
4 g of Example 23
0.12 g of 50 percent triethanolamine (TEA) in water
As 10 grams of the composition of Preparative Example 6 was stirred with a high shear impeller 4 grams of Example 23 was slowly added and mixed for 1 minute. The gel was neutralized with addition of 0.12 grams of 50 percent TEA while stirring. The gel thickened and stirring was discontinued.

Cosmetic Example 1

An oil in water emulsion for mascara was prepared using the specific components and amounts in weight percent for Phase A and Phase B listed in Table 1. Phase A and Phase B were heated to 90° C. with continuous mixing in separate vessels. Phase B was added to phase A and homogenized using a high shear mixer. After cooling, the resulting paste provides a flake-, smudge-, and water-resistant mascara.

TABLE 1

Oil in water emulsion for mascara

| Component | Amount (weight percent) |
| --- | --- |
| Phase A: | |
| Carnuba Wax | 10.00 |
| Isopropyl myristate | 2.00 |
| Glyceryl stearate | 3.00 |
| Stearic acid | 5.00 |
| Polymer solution from Preparative Example 1 | 10.00 |
| Black iron oxide pigment | 10.00 |
| Phase B: | |
| Deionized water | 58.15 |
| Polyvinylpyrrolidone | 1.00 |
| Hydroxyethyl cellulose[1] | 0.20 |
| Triethanol amine | 0.65 |

[1]commercially available as Natrosol type 99-250LR CS from Aqualon (a division of Hercules Incorporated, Wilmington, Delaware)

Cosmetic Example 2

A styling shampoo was prepared by charging 32 parts of deionized water into a vessel and dispersing 1 part of guar gum (commercially available as "Jaguar 8111" from Rhone Poulenc, Inc., Cranberry, N.J.) into it with moderate stirring. Then 16 parts of the polymer solution from Preparation Example 1 was charged into the vessel followed by 35.7 parts aqueous ammonium lauryl sulfate solution (commercially available as "Standapol A" from Henkel Corporation, Cincinnati, Ohio) and 11.4 parts of aqueous cocamidopropyl betaine solution (commercially available as "Icronam 30" from Croda, Inc., Parsippany, N.J.). The resulting moderate viscosity solution provided a high lather shampoo that imparted "volumizing" properties to hair after rinsing and drying.

Cosmetic Example 3

A clear nail lacquer was prepared by adding 20 parts of the polymer solution from Preparation Example 1 to 80 parts of a solution of nitrocellulose, toluene-sulfonamide formaldehyde resin, dibutyl phthalate, camphor, and hydrolyzed protein in a mixed solvent system of butyl acetate, ethyl acetate, toluene, and isopropanol (sold as Mystic Nails™ brand nail hardener from Magic Nails, Inc., Staten Island, N.Y.) After mixing, the resulting clear solution shows good wet out and leveling tendencies and is fast drying providing a tack-free durable water-repellant clear coating.

Cosmetic Example 4

An oil in water emulsion for use as a foundation, eye shadow, or sunscreen (SPF value adjusted by adding organic sunscreen agents) was prepared using the specific components and amounts in weight percent for Phase A and Phase B listed in Table 2. Phase A and Phase B were heated to 80° C. with continuous mixing in separate vessels. Phase B was added to phase A and homogenized using a high shear mixer.

After the emulsion formed it was cooled to 40° C. using gentle mixing.

TABLE 2

Oil in water emulsion for foundation, eye shadow, or sunscreen

| Components | Amount (weight percent) |
| --- | --- |
| Phase A | |
| Water | 48.40 |
| Propylene glycol | 9.73 |
| Polysiloxy linoleyl pyrrolidone phospholipid[1] | 2.10 |
| Triethanol amine | 1.00 |
| Talc | 1.90 |
| Magnesium sulfate | 1.90 |
| Titanium Dioxide | 1.00 |
| Black Iron Oxide Pigment | 1.00 |
| Methyl paraben | 0.14 |
| Phase B | |
| C12–15 alkyl benzoate[2] | 16.40 |
| Stearic acid | 1.90 |
| Polyoxyethylene (4) lauryl ether[3] | 0.40 |
| Polydimethylsiloxane 100 cst | 1.00 |
| Polymer Solution from Preparation Example 1 | 9.90 |
| Tea tree Oil | 0.20 |
| Vitamin E Acetate | 0.05 |

[1]Commercially available as Monasil PLN from Mona Industries, Paterson, NJ.
[2]Commercially available as FINSOLV TN from Fintex, Inc., Elmwood Park, NJ.
[3]Commercially available as ICI BRIJ ™ 30 from Uniquema, Wilmington, DE.

Cosmetic Example 5

A water in oil emulsion was prepared using the specific components and amounts in weight percent for Phase A and Phase B listed in Table 3. Phase A and Phase B were heated to 80° C. with continuous mixing in separate vessels. Phase B was added to phase A and homogenized using a high shear mixer.

After the emulsion formed it was cooled to 40° C. using gentle mixing.

TABLE 3

Water in oil emulsion

| Components | Amount (weight percent) |
| --- | --- |
| Phase A | |
| Cyclotetrasiloxane | 34.70 |
| Polymer Solution from Preparation Example 1 | 06.30 |
| Mineral Oil | 09.68 |
| Sorbitan trioleate[1] | 03.73 |
| Sorbitan monolaurate[2] | 02.26 |

TABLE 3-continued

Water in oil emulsion

| Components | Amount (weight percent) |
|---|---|
| Phase B | |
| Water | 42.84 |
| Dipropylene glycol | 01.99 |
| Methyl paraben | 00.20 |

[1]Commercially available as ICI Span ™ 85 from Uniquema.
[2]Commercially available as ICI Arlacel ™ 85 from Uniquema.

Cosmetic Example 6

Mixtures of various waxes, solvents (both volatile and non-volatile), pigments, fillers, slip agents, silicones, siloxy silicates, and polymers were combined for use in lipstick, anhydrous mascara, eye shadow, blush/rouge, and the like. To one skilled in the art changing the ratio of the various ingredients will moderate the physical properties of the formulation to impart the desired feel and performance of the resulting cosmetic. Tables 4, 5, and 6 contain several simple examples of formulations containing the polymer from Preparation Example 1. Table 4 contains two runs using different solvents. Table 5 contains five runs using different slip agents. Table 6 contains two runs using different polymers in combination with the polymer from Preparation Example 1. The components were charged into a closed clean vessel, heated to a temperature (depending on the waxes used) of less than 100° C. and thoroughly mixed until a uniform composition was achieved. The composition was then molded and packaged as desired.

TABLE 4

Examples for lipstick, anhydrous mascara, eye shadow, blush/rouge using different solvents

| Component | Run 1: Amount (weight percent) | Run 2: Amount (weight percent) |
|---|---|---|
| Waxes: | | |
| Carnuba wax | 3.63 | 3.63 |
| Ozokerite ceresin | 9.05 | 9.05 |
| Paraffin wax | 5.43 | 5.43 |
| Bees wax | 3.63 | 3.63 |
| Nonvolatile oils: | | |
| Sunflower oil | 6.20 | 6.20 |
| Isopropyl myristate | 8.83 | 8.83 |
| Volatile silicon solvent: | | |
| Cyclopenta-siloxane | 17.54 | 17.54 |
| Colorant: | | |
| Black Iron oxide pigment | 17.14 | 17.14 |
| Nonvolatile silicon solvent | | |
| Phenylmethicone | 19.04 | |
| Volatile organic solvents: | | |
| Permethyl ™ 97A[1] | | 18.89 |
| Polymer Solution from Preparation Example 1 | 9.52 | 9.54 |

[1]Commercially available from Permethyl Specialties, LLC.

TABLE 5

Examples for lipstick, anhydrous mascara, eye shadow, blush/rouge using different slip agents

| Component | Run 3: Amount (weight percent) | Run 4: Amount (weight percent) | Run 5: Amount (weight percent) | Run 6: Amount (weight percent) | Run 7: Amount (weight percent) |
|---|---|---|---|---|---|
| Waxes: | | | | | |
| Carnuba wax | 4.09 | 4.09 | 4.09 | 4.09 | 3.96 |
| Ozokerite ceresin | 10.21 | 10.21 | 10.21 | 10.21 | 9.89 |
| Paraffin wax | 6.13 | 6.13 | 6.13 | 6.13 | 5.94 |
| Bees wax | 4.09 | 4.09 | 4.09 | 4.09 | 3.96 |
| Nonvolatile oils: | | | | | |
| Sunflower oil | 7.00 | 7.00 | 7.00 | 7.00 | 6.79 |
| Isopropyl myristate | 9.96 | 9.96 | 9.96 | 9.96 | 9.65 |
| Volatile silicon solvent: | | | | | |
| Cyclopentasiloxane | 19.80 | 19.80 | 19.80 | 19.80 | 19.18 |
| Colorant: | | | | | |
| Black Iron Oxide Pigment | 19.35 | 19.35 | 19.35 | 19.35 | 18.75 |
| Slip Agents: | | | | | |
| Boron Nitride | 3.23 | | | | 1.56 |
| Styrene/divinyl benzene copolymer spheres[1] | | 3.23 | | | 1.56 |
| Polymethylmethacrylate spheres[2] | | | 3.23 | | 1.56 |
| Mica | | | | 3.23 | 1.56 |
| Polymer Solution from Prep Example 1 | 16.13 | 16.13 | 16.13 | 16.13 | 15.63 |

[1]Commercially available as Ganzpearl GS-0605 from Presperse Inc., Piscataway, NJ.
[2]Commercially available as MBX-4C from US Cosmetics Corporation, Dayville, CT.

TABLE 6

Examples for lipstick, anhydrous mascara, eye shadow, blush/rouge using different polymers

| Components | Run 8 | Run 9 | Run 10 |
|---|---|---|---|
| Waxes: | | | |
| Carnuba wax | 3.52 | 3.43 | 3.52 |
| Ozokerite ceresin | 8.79 | 8.56 | 8.79 |
| Paraffin wax | 5.28 | 5.13 | 5.28 |
| Bees wax | 3.52 | 3.43 | 3.52 |
| Nonvolatile oils: | | | |
| Sunflower oil | 6.03 | 5.87 | 6.03 |
| Isopropyl myristate | 8.58 | 8.35 | 8.58 |
| Volatile silicon solvent: | | | |
| Cyclopentasiloxane | 17.05 | 16.59 | 17.05 |
| Colorant: | | | |
| Black Iron Oxide Pigment | 16.66 | 16.21 | 16.66 |
| Slip Agents: | | | |
| Boron Nitride | 1.39 | 1.35 | 1.39 |
| Styrene/divinyl benzene copolymer spheres[1] | 1.39 | 1.35 | 1.39 |
| Polymethyl-methacrylate spheres[2] | 1.39 | 1.35 | 1.39 |
| Mica | 1.39 | 1.35 | 1.39 |
| Polymers: | | | |
| Polyacrylate-g-polydimethylsiloxane (23 percent solids in cyclopentasiloxane)[3] | 11.11 | 6.76 | |
| Polyvinylpyrrolidone/eicosene copolymer[4] | | 6.76 | 11.11 |
| Polymer Solution from Preparation Example 1 | 13.89 | 13.51 | 13.89 |

[1]Commercially available as Ganzpearl GS-0605 from Presperse Inc., Piscataway, NJ.
[2]Commercially available as MBX-4C from US Cosmetics Corporation, Dayville, CT.
[3]Commercially available as 3M ™ Silicones "Plus" Polymer SA 70 from 3M Company, St. Paul, MN.
[4]Commercially available as GANEX ™ V220 from ISP Technologies, Wayne, NJ.

The polymer from Preparation Example 1 imparted superior adhesion properties of the formulations to the skin/lips which reduced the tendency of the material to transfer to other surfaces.

What is claimed is:

1. A composition for application to the skin, comprising:
   a) 1–40% of siloxane-containing polymer comprising at least one vinyl containing alkylsiloxysilane and an addition polymerizable comonomer, wherein the vinyl containing alkylsiloxysilane has the following formula:

$$CH_2=C(R^1)COOR^2SiR^3R^4R^5$$

where $R^1$=H, $CH_3$, or $CH_2COOR'$ and where $R'=R^2SiR^3R^4R^5$;
where $R^2$=alkyl ($C_1$ to $C_4$) or $CH_2CH(OH)CH_2$;
where $R^3$, $R^4$, or $R^5$=$OSi(Y)_3$ or alkyl ($C_1$ to $C_6$) and at least one of $R^3$, $R^4$, or $R^5$=$OSi(Y)_3$;
where Y=$CH_3$ or $OSi(Z)_3$; and
where Z=$CH_3$;
   b) 60–99% of an Alkane-Based Siloxy Polymer Reaction Solvent; and
   c) 0–15% of adjuvant;
wherein the composition is in the form of a solution.

2. The composition of claim 1, wherein said Alkane-Based Siloxy Polymer Reaction Solvent is selected from the group consisting of $C_5$–$C_{12}$ straight, branched or cyclic alkanes.

3. The composition of claim 1, wherein said Alkane-Based Siloxy Polymer Reaction Solvent is selected from the group consisting of hexane, heptane, octane, nonane, and mixtures thereof.

4. The composition of claim 1, wherein said Alkane-Based Siloxy Polymer Reaction Solvent is a blend of a first solvent selected from the group consisting of hexane, heptane, octane, nonane and mixtures thereof and a second solvent selected from the group consisting of decane, undecane, dodecane, and mixtures thereof.

5. A sprayable composition of claim 1, comprising
   a) 2–10% of said siloxane-containing polymer;
   b) 86–93% of said Alkane-Based Siloxy Polymer Reaction Solvent; and
   c) 2–4% adjuvants.

6. A sprayable composition of claim 1, comprising:
   a) 6–10% of said siloxane-containing polymer;
   b) 86–93% of said Alkane-Based Siloxy Polymer Reaction Solvent; and
   c) 2–4% adjuvants.

7. A method of making a siloxane containing polymer comprising vinyl containing alkylsiloxysilanes or as co-, ter- or multi component polymers including other polymerizable monomers, which method comprises undertaking the polymerization in an Alkane-Based Siloxy Polymer Reaction Solvent so that the reaction provides a composition in the form of a Solution having a polymer content greater than 15% by weight.

8. A gel composition for application to skin, comprising:
   a) 1–15% siloxane-containing polymer of claim 1;
   b) 10–25% Alkane-Based Siloxy Polymer Reaction Solvent;
   c) 0–10% adjuvants;
   d) 38–88.5% water and
   e) 0.5–2 emulsifier.

9. The composition of claim 1, wherein said Alkane-Based Siloxy Polymer Reaction Solvent is present at 60–98.5% and said adjuvant is present in an effective amount to impart color to the skin of a user.

10. The composition of claim 1, wherein said Alkane-Based Siloxy Polymer Reaction Solvent is present at 60–98.5% and said adjuvant is present in a medically effective amount.

11. The composition of claim 1, wherein said Alkane-Based Siloxy Polymer Reaction Solvent is present at 60–98.5% and said adjuvant is a sunscreen that is present in an effective amount to provide sunscreen protection.

12. The composition of claim 1, wherein said vinyl containing alkylsiloxysilane is selected from the group consisting of 3-methacryloyloxypropyltris(trimethylsiloxy)silane, 3-methacryloyloxypropylpentamethyldisiloxane, 3-methacryloyloxypropylbis(trimethylsiloxy)methylsilane, 3-acryloyloxypropylmethylbis(trimehtylsiloxy)silane, and 3-acryloyloxypropyltris(trimethylsiloxy)silane.

* * * * *

UNITED STATES PATENT AND TRADEMARK OFFICE
CERTIFICATE OF CORRECTION

PATENT NO. : 6,383,502 B1
DATED : May 7, 2002
INVENTOR(S) : Dunshee, Wayne K.

It is certified that error appears in the above-identified patent and that said Letters Patent is hereby corrected as shown below:

Column 7,
Line 37, "As" should read -- as --.

Column 9,
Line 40, "0.5g" should read -- 0.50g --.
Line 66, "0.10g Vitamin E" should read -- 0.1g Vitamin E --.

Signed and Sealed this

Fourth Day of February, 2003

JAMES E. ROGAN
*Director of the United States Patent and Trademark Office*